United States Patent [19]

Borody

[11] Patent Number: 5,476,669
[45] Date of Patent: * Dec. 19, 1995

[54] METHOD FOR TREATMENT OF GASTRO INTESTINAL DISORDERS

[75] Inventor: Thomas J. Borody, Five Dock, Australia

[73] Assignees: Examed Australia Pty. Ltd.; Ostapat Pty. Limited; Gastro Services Pty. Limited; Capability Services Pty. Limited, all of New South Wales, Australia

[*] Notice: The portion of the term of this patent subsequent to Mar. 23, 2010, has been disclaimed.

[21] Appl. No.: 937,421

[22] Filed: Aug. 31, 1992

Related U.S. Application Data

[63] Continuation of Ser. No. 466,310, filed as PCT/AU55/00379, Sept. 29, 1988, Pat. No. 5,196,205.

[30] Foreign Application Priority Data

Oct. 12, 1987 [AU] Australia .................................. PI4838
Dec. 18, 1987 [AU] Australia .................................. PI5985
Mar. 30, 1988 [AU] Australia .................................. PI7513

[51] Int. Cl.[6] .................. A61K 33/24; A61K 31/65; A61K 31/43; A61K 31/44
[52] U.S. Cl. .................. 424/653; 514/154; 514/199; 514/338; 514/370; 514/398; 514/400; 514/471; 514/925
[58] Field of Search .................. 424/653; 514/925, 514/154, 199, 398, 400, 471, 370, 338

[56] References Cited

U.S. PATENT DOCUMENTS 4,535,081 8/1985 Kadin .................................. 514/258
4,839,353 6/1989 Hosoi et al. .......................... 514/212

OTHER PUBLICATIONS

McNulty et al., *Campylobacter III, Proceedings of the Third International Workshop of Campylobacter Infection*, Jul. 7–10, 1985, Abstract #099, pp. 163–164.

McNulty et al., *Antimicrobial Agents and Chemotherapy*, vol. 28, No. 6, pp. 837–838, Dec. 1985.

D. Y. Graham, G. M. Lew, P. D. Klein, D. G. Evans, D. J. Evans, G. A. Saced, and H. M. Malary, "Effect of Treatment of Helicobacter pylori Infection on the Long–term Recurrence of Gastric or Duodenal Ulcer", Annals of Internal Medicine, vol. 116, No. 9, pp. 705 to 707 (May 1, 1992).

T. J. Borody, S. Brandl, P. Andrews, E. Jankiewicz, and N. Ostapowicz, "Helicobacter Pylori–Negative Gastric Ulcer" Centre for Digestive Diseases, Sydney, Australia (accepted for publication, Amer. J. Gastroenterology), 1992.

*Primary Examiner*—Raymond Henley, III
*Assistant Examiner*—William R. A. Jarvis
*Attorney, Agent, or Firm*—Ronald P. Kananen

[57] ABSTRACT

A method is disclosed for preventing the recurrence of duodenal ulcer associated with *Campylobacter pylori* (*Helicobacter pylori*) infection in a patient suffering from duodenal ulcer disease associated with *Campylobacter pylori* infection by administering a pharmaceutically acceptable bismuth compound, a first antibiotic selected from the group consisting of tetracycline and penicillins, and a second antibiotic which is metronidazole.

34 Claims, 1 Drawing Sheet

1

METHOD FOR TREATMENT OF GASTRO INTESTINAL DISORDERS

This application is a continuation division of application Ser. No. 07/466,310 filed as PCT/AU88/00379, Sept. 29, 1988, now U.S. Pat. No. 5,196,205.

TECHNICAL FIELD

This invention relates to pharmaceutical compositions and therapeutic methods for eradication and/or prevention of recurrence of gastrointestinal disorders associated with infection by *Campylobacter Pylori*

BACKGROUND ART

*C. pylori* is a recently described bacterium found to cause chronic histological gastritis. Its causal role in peptic ulceration is less clear and even less so in non-ulcer dyspepsia. Its role could be more effectively studied if effective therapy for its eradication were devised.

Until recent times, *C. pylori* has been found to be difficult to eradicate using known chemotherapeutic agents. Although many antibiotics can suppress *C. pylori* growth in vitro, in vivo the mucosal concentration appears to be inadequate and penetration of the usual gastric mucus layer poor. Hence, development of an adequate in vivo eradication method for chronic *C. pylori* infection has been difficult. Moreover, adequate prediction of in vivo results cannot be predicted from in vitro work.

European Patent Application No. 206,625 and Australian Patent Application No. 59026/86 describe the use of bismuth together with a single antibiotic for the treatment of *C. pylori*. However, bismuth alone achieves low (30 to 70%) initial clearance rates for *C. pylori* and recurrence of the infection approaches 100% by twelve months post therapy. Bismuth together with a single antibiotic, namely amoxicillin, appears to be relatively effective as a short term means of reducing the symptoms but it is now clear that the use of bismuth together with a single antibiotic frequently fails to eradicate the infection and has a high rate of infection recurrence (Rauws, Erik A. J. et al; Gastro-enterology, 1988; 94: 33–40).

DISCLOSURE OF THE INVENTION

The present inventor has now found that the use of a multi antibiotic therapy not only results in a high initial clearance rate of *C. pylori*, of the order of greater than 90%, but also leads to a high eradication rate where most patients remain free of infection for more than twelve to eighteen months. It now seems that therapeutic success measured at eight weeks biopsy (post treatment) should be termed as clearance only whilst the term "eradication" should be used in the context of patients who remain free of *C. pylori* infection for more than twelve months post treatment.

The present inventor has also found that *C. pylori* is not only associated with gastritis but is also causally associated with peptic ulcer including duodenal, pre-pyloric, gastric, oesophageal and marginal ulcer and consequently the novel therapy for eradication of *C. pylori* described in the present invention is useful in the treatment of peptic ulcer as well as non-ulcer dyspepsia. Moreover, the novel therapy of the present invention is useful in the treatment of oesophageal reflux, reflux oesophagitis as well as asymptomatic carrier states.

In one broad form the present invention provides a pharmaceutical composition for the treatment of gastro intestinal disorders associated with *C. pylori* infections comprising a pharmaceutically acceptable bismuth compound, a first antibiotic or antimicrobial agent and a second antibiotic or antimicrobial agent.

In a further form the invention provides a sequential pack comprising a first pharmaceutical composition in unit dosage form adapted and presented in said pack for a first administration period of 3 to 36 days, said first composition comprising a pharmaceutically acceptable bismuth compound and a first antibiotic or antimicrobial agent together with a second pharmaceutical composition comprising a second antibiotic or antimicrobial agent in unit dosage form adapted and presented in said pack for a second administration period different from said first administration period.

The invention also provides a sequential pack for the administration of at least two pharmaceutical compositions comprising a first composition which comprises a pharmaceutically acceptable bismuth compound, a first antibiotic or antimicrobial agent and a second antibiotic or antimicrobial agent, in unit dosage form adapted and presented for a first administration period of 3 to 36 days, together with a second pharmaceutical composition which comprises an acid suppressant for ulcer treatment in unit dosage form adapted and presented for a second administration period of 3 to 36 days prior to or overlapping with the initial part of said first administration period.

Preferably, the first antibiotic or antimicrobial agent is selected from one or more of tetracyclones, penicillins, quinolones, cephalosporins, furazolidones, lincosamides, nitrofurantoins and/or polypeptides. Preferably, the second antibiotic or antimicrobial agent is selected from one or more of quinolones, furazolidones, nitrofurantoins, metronidazoles, and/or cephalosporins.

More preferably the first antibiotic or antimicrobial agent is selected from tetracyclines and/or penicillins and the second antibiotic is a metronidazole.

The tetracyclines include tetracycline, oxytetracycline, doxycycline, demeclocycline, methacycline and minocycline.

The penicillins include penicillin G, penicillin V, oxacillin, nafcillin, ampicillin, amoxicillin, cloxacillin and carbenicillin.

The metronidazoles include metronidazole and tinidazole.

Rifanpin, trimethoprim and/or nalidixic acid may also be used.

The cephalosporins include cephalexin (Keflex), cefaclor, cephapirin, cephradine and cefadroxil as well as second and third generation cephalosporins.

The polypeptide antibiotics include polymyxin B, bacitracin, colisin sulfate and/or spectinomycin HCl.

Quinolones Include ciprofloxacin, norfloxacin and ofloxacin.

Lincosamides include lincomycin and clindamycin.

Whilst it is preferred that the first and second antibiotics or antimicrobial agents are selected from different classes, they may be selected from within the one class. Moreover, a third or more antibiotics may be included in the methodology and compositions of the invention; e.g. amoxicillin, tetracycline and metronidazole. Keflex is also preferably used as one of the first or second antibiotics or as a further antibiotic.

Bismuth compounds suitable in the present invention include those selected from the group consisting of bismuth aluminate, bismuth subcarbonate, bismuth subcitrate, bismuth titrate, tripotassium dicitrato bismuthate, bismuth subgalate, bismuth subnitrate, bismuth tartrate, bismuth salicylate, bismuth subsalicylate, and mixtures thereof. Bismuth citrate, bismuth subcitrate, tripotassium dicitrato bismuthate, bismuth tartrate, bismuth subsalicylate, and mixtures thereof are preferred bismuth salts for use in this invention. The bismuth useful herein may be administered alone, or in combination with other pharmaceutically-acceptable components, in a bismuth-containing composition. A variety of such compositions containing bismuth salts are commercially-available, including, for example, DeNoi, containing tripotassium dicitrato bismuthate sold by Gist-Brocades N.V.), Noralac, containing bismuth aluminate, alginic acid, and magnesium carbonate (manufactured by North American Pharmaceuticals), Roter bismuth, containing bismuth subnitrate (sold by Roter Laboratories), Fensobar Polvo, containing bismuth subcarbonate among other materials (manufactured by USV Pharmaceutical Corporation), and Pepto-Bismol, containing bismuth subsalicylate (sold by The Procter & Gamble Company).

In a preferred form of the present invention there is provided a method of treating gastro intestinal infections associated with *C. pylori* which comprises administering an effective amount of a pharmaceutically acceptable bismuth compound in combination with a tetracycline and/or a penicillin and a metronidazole.

In a further aspect of the present invention there is provided a capsule for oral administration to patients suffering from gastro intestinal infections associated with *C. pylori* wherein said capsule includes a pharmaceutically acceptable bismuth compound together with a first antibiotic and a second antibiotic wherein said capsule is adapted to release said bismuth within the stomach of the recipient and wherein at least said first antibiotic and preferably also said second antibiotic is microencapsulated so that said first and optionally said second antibiotic is released within the gastro intestinal tract after said stomach.

In a preferred form of this aspect of the invention there is provided a capsule containing an effective amount of a pharmaceutically acceptable bismuth compound together with enteric coated micro-spherules of an antibiotic of the tetracycline class or penicillin class which capsule also contains an effective amount of a second antibiotic selected from the metronidazole class which second antibiotic is optionally provided in enteric coated micro-spherule form.

In a further aspect of the present invention the methodology uses the treatment regimen comprising the combination of pharmaceutically acceptable bismuth compound in combination with a first antibiotic and a second antibiotic for between three to twenty-eight days. Preferably the treatment is combined with the administration of an acid suppress such as an histamine$_2$ antagonist such as cimetidine, ranitidine or famotidine to effect symptomatic relief and ulcer epithelialization. This is followed by the combination of the bismuth and first and second antibiotic therapy. Preferably the histamine$_2$ antagonist is administered for three to twenty-eight days followed by a three to twenty-eight day therapy of the bismuth/antibiotics combination. Other acid suppressants may be used instead of an histamine$_2$ antagonist such as benzimidazole or prostoglandins. Alternatively, the histamine$_2$ blocker or other acid suppressant can be combined with the pharmaceutical composition of the present invention.

The present invention also provides a sequence presented pack suitable for therapy for gastro intestinal disorders associated with *C. pylori* infection which combines a pharmaceutically acceptable bismuth compound together with a first antibiotic and a second antibiotic and optionally further antibiotics so that said treatment regimen can be adapted for individual patient needs. Optionally the sequence presented pack may also include an initial therapy comprising an acid suppressant such as a histamine$_2$ antagonist or a K/Na ATP-ase inhibitor such as omeprazole and may be combined with mucus disrupting agents such as carbocysteine, n-acetylcysteine, corticosteroids or bisolvon. It should be noted that the pharmaceutical composition comprises at least two antibiotics but further antibiotics may be selectively added in difficult cases or where resistant strains and/or multiple strains present a more resistant problem.

In the composition and methodology of the present invention, preferably from 5 to 5000 mg, more preferably 50 to 250 mg of a pharmaceutically acceptable bismuth compound is used together with from 5 to 10000 mg, more preferably 50 to 500 mg of a first antibiotic together with from 5 to 10000 mg, more preferably 50 to 250 mg of a second antibiotic.

Preferably the invention provides a pharmaceutical composition containing from 50 to 250 mg of a colloidal bismuth in pharmaceutically acceptable form, 50 to 500 mg of tetracycline or a penicillin (e.g. amoxicillin) type antibiotic and 50 to 250 mg of a metronidazole type antibiotic such as metronidazole or tinidazole. Preferably the tetracycline or penicillin is microencapsulated to prevent bismuth chelation at high pH.

In a further aspect the invention provides a sequential pack comprising an antimicrobial pharmaceutical composition in unit dosage form adapted for an administration period of three to thirty-six days, said antimicrobial composition comprising a pharmaceutically acceptable bismuth compound, at least a first antibiotic and at least a second antibiotic, together with a palliative pharmaceutical composition in unit dosage form adapted and presented for a three to thirty-six day administration period prior to, or overlapping with the initial part of the administration period of said antimicrobial pharmaceutical composition wherein said palliative pharmaceutical composition comprises a therapeutic agent such as an acid suppressant, adapted for ulcer treatments.

In a further aspect the invention provides a sequential pack comprising a first pharmaceutical composition in unit dosage form adapted for an administration period of three to thirty six days, said composition comprising a pharmaceutically acceptable bismuth compound and at least a first antibiotic, together with a second pharmaceutical composition in unit dosage form comprising a second antibiotic adapted for administration for a period different to said administration period of said first pharmaceutical composition. Preferably the pack further comprises a palliative pharmaceutical composition in unit dosage form presented in said pack in a 3 to 36 day administration period which is prior to or overlaps with the initial part of the administration period of said first pharmaceutical composition wherein said palliative pharmaceutical composition comprises a therapeutic agent, such as an acid suppressant, adapted for ulcer treatment.

BEST MODES OF CARRYING OUT THE INVENTION

The methodology and treatment described above is useful in the treatment of disorders associated with *C. pylori* which include duodenal ulcer, pre-pyloric ulcer, gastric ulcer, oesophageal ulceration, reflux oesophagitis with or without ulceration, bile-reflux "gastritis" non ulcer dyspepsia associated with *C. pylori* gastritis and/or asymptomatic carrier state.

Whilst tablets of capsules of the pharmaceutical composition of the present invention are preferred, sachets or syrups or other orally ingestible forms of the compositions are also included within the scope of the present invention.

Figure 1:
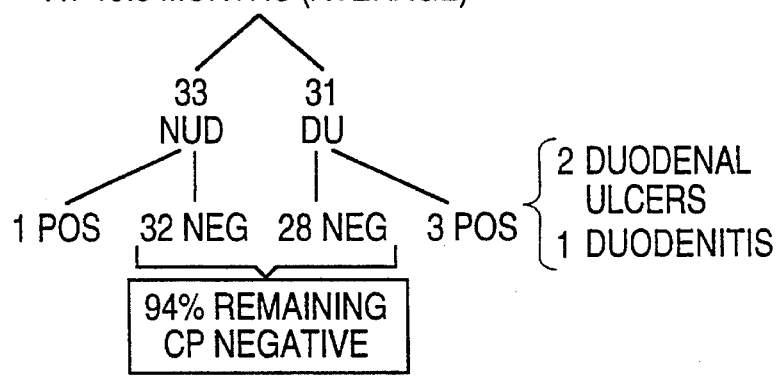
FIG. 1 illustrates results of treatment according to the present invention in 64 to 100 patients at an average of 19.3 months after treatment.
Figure 2:
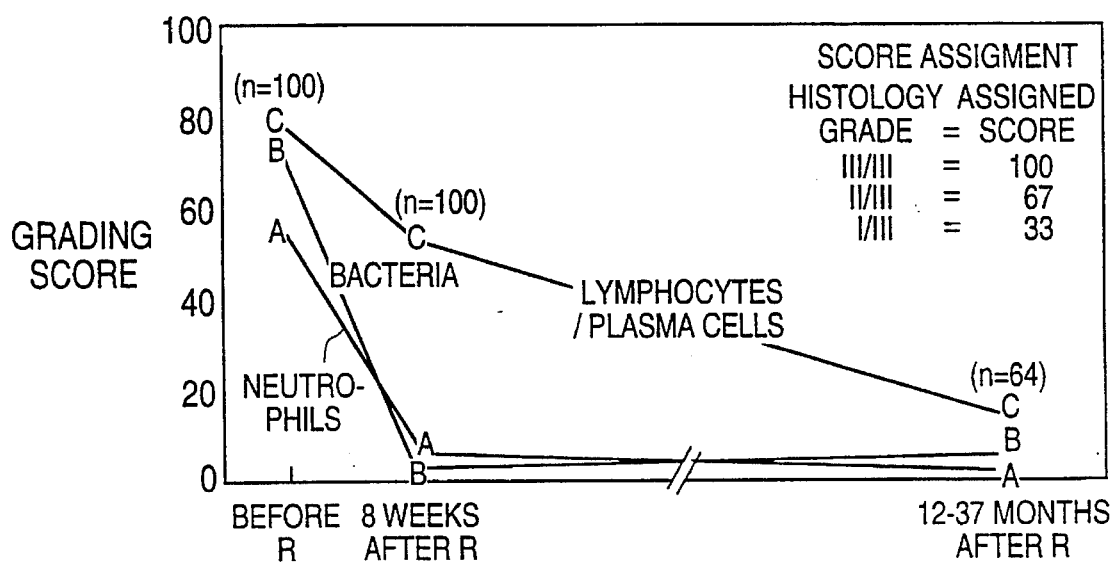
FIG. 2 illustrates histologic grading before and after treatment with the treatment of the present invention.

The invention will be further described with reference to the following test procedure of the Example and accompanying Figures wherein FIG. 1 shows the results of treatment of the present invention in 64 out of 100 patients at an average of 19.3 months post treatment and FIG. 2 shows the histologic grading pre and post treatment with the treatment of the present invention.

EXAMPLE

Test Procedure

Patients aged 19 to 79 years (M:F=47:53) with symptoms of dyspepsia lasting three months or more referred for endoscopy were entered. Only patients positive for *C. pylori* with either duodenal ulcer or non-ulcer dyspepsia were entered into the study. Patients were deemed to have non-ulcer dyspepsia if, in the absence of ulcer or other disease, they complained of food related epigastric discomfort or pain, bloating, belching, nausea, a feeling of fullness or heartburn. Patients with duodenal ulcer were entered into the treatment protocol only after ulcer treatment with either four weeks of ranitidine (300mg/day) or cimetidine (800mg/day), known not to influence *C. pylori*. Exclusion criteria included coagulopathy, antibiotic use within two weeks of endoscopy, presence of oesophageal varices, previous gastrectomy, neoplasm, systemic disease or allergy preventing use of the medications. Gastric ulcer patients were excluded to form a separate study. Of 122 patients entered in the study, 112 completed the triple chemotherapy adequately. Of these, 100 consecutive re-endoscoped patients became available for analysis of results at eight weeks after commencement of treatment and constitutes the short term follow up group. Ten patients did not complete the treatment due to failure to follow up (4), nausea (2), clostridium difficile-positive diarrhoea (1), allergy (2), and oral moniliasis (1), At 12 to 37 months after *C. pylori* eradication therapy CP-negative patients at eight weeks from the pilot studies and the abovementioned group were invited for re-examination by gastroscopy. Of the entire cohort 64 patients returned for examination and constitute the long term follow up group.

Gastroscopy

All examinations were carried out by the same endoscopist. Two biopsy specimens were taken from the gastric antrum and one from the body. One antral specimen was placed in a microtitre tray containing buffered urea and an indicator to detect rapidly presence of *C. pylori* urease activity. The other specimens were placed in 10% buffered formalin for histological examination. No bacterial cultures were carried out.

Histological Assessment

Paraffin sections of tissues fixed in formalin were stained with haematoxylin and eosin to grade severity of histological gastritis and with Marthin-Starry silver stain to grade *C. pylori* density. Grading was based on density of lymphocyte/plasma cell (chronic), neutrophil (active) infiltration, or presence of *C. pylori* from 0 to III as previously described.

Specimens were graded by the same consultant histopathologist without knowledge of patients' details.

Medication

Except for eight patients allergic to tetracycline, all subjects received a combination of colloid bismuth subcitrate (108 mg chew-tablets q.i.d.), tetracycline HCl (500 mg q.i.d.) for four weeks, together with metronidazole (200 mg q.i.d.) for the first ten days. Amoxicillin (500 mg q.i.d.) was substituted for tetracycline in the eight allergic patients. Patients and endoscopist were not blinded to the treatment regimen. Patients were asked if they had completed the medication as requested but no tablet count was attempted.

Assessment of Symptoms

For patients with idiopathic non-ulcer dyspepsia (NUD) a questionnaire form was developed and administered six months following clearance of *C. pylori*. Global assessment of percent improvement in these patients is reported below. In duodenal ulcer patients symptom improvement or disappearance was recorded.

RESULTS

Clearance of *C. Pylori* at eight weeks

Of the 100 consecutive available patients treated for *C. pylori*, 94 were negative on urease testing and histology at eight weeks after commencement of chemotherapy (See Table 1). The six patients remaining positive at eight weeks claimed to have taken their medication as directed.

Long Term Clearance of *C. pylori*

Follow up gastroscopic biopsies were obtained in 64 patients (M:F= 36:28) at 12 to 37 months after original triple chemotherapy (mean=19.3 months), and results shown in FIG. 1. These patients were drawn from the 94 who remained CP negative at eight weeks post therapy and from a small pilot study carried out some months earlier. Of these 64, paid recalled volunteers who resubmitted to gastroscopic biopsy, 33 had been originally diagnosed as having non-ulcer dyspepsia while 28 had endoscopically-proven duodenal ulcer. At follow up overall 60 or 947. remained free of *C. pylori* infection at the 19.3 months. One of the 33 NUD patients was again positive for the bacteria while three of 31 patients originally with duodenal ulcer were CP positive. In the latter three patients, two again had re-ulcerated while the other patient had pronounced duodenitis. All 28 patients who remained free of *C. pylori* maintained their ulcers endoscopically healed. They were on no maintenance therapy and were free of ulcer-like symptoms.

In NUD patients, as a global assessment in the 32 cleared patients, 25/32 (78%) reported a "50% or more improvement" over their initial symptom scores. On the other hand in four other patients with NUD in spite of CP eradication and reversal of histologic gastritis no improvement in dyspeptic symptoms occurred. An unexpected finding in four of 15 patients who initially had linear oesophageal ulceration, was total healing and disappearance of the ulcers after *C. pylori* eradication. No appreciable weight change had occurred in these patients and the improvement could not be ascribed to any other medica therapy.

TABLE 1

| Patient | Age | M/F | C. pylori at start of treatment | C. pylori 8 wks past therapy |
|---|---|---|---|---|
| 1 N.U.D | 65 | F | +ve | −ve |
| 2 D.U | 59 | M | +ve | −ve |
| 3 N.U.D | 62 | F | +ve | −ve |
| 4 N.U.D | 63 | M | +ve | −ve |
| 5 N.U.D | 35 | M | +ve | −ve |
| 6 P.P.U | 74 | F | +ve | −ve |
| 7 G.U 3 | 40 | F | +ve | +ve* |
| 8 D.U | 65 | M | +ve | −ve |
| 9 2 D.U | 55 | F | +ve | −ve |
| 10 D.U | 60 | M | +ve | +ve* |
| 11 N.U.D | 60 | M | +ve | −ve |
| 12 N.U.D | 66 | M | +ve | −ve |
| 13 P.P.U | 59 | M | +ve | −ve |
| 14 N.U.D | 28 | F | +ve | −ve |
| 15 P.P.U | 36 | M | +ve | −ve |
| 16 D.U | 22 | M | +ve | −ve |
| 17 D.U | 42 | F | +ve | −ve |
| 18 N.U.D | 65 | F | +ve | −ve |
| 19 D.U | 32 | M | +ve | −ve |
| 20 D.U | 65 | M | +ve | −ve |
| 21 N.U.D | 61 | M | +ve | −ve |
| 22 D.U | 29 | F | +ve | +ve* |
| 23 N.U.D | 29 | M | +ve | −ve |
| 24 N.U.D | 30 | M | +ve | −ve |
| 25 D.U | 74 | M | +ve | −ve |
| 26 N.U.D | 42 | M | +ve | −ve |
| 27 N.U.D | 38 | M | +ve | +ve* |
| 28 P.P.U | 51 | F | +ve | −ve |
| 29 N.U.D | 26 | M | +ve | −ve |
| 30 D.U | 44 | F | +ve | −ve |
| 31 D.U | 50 | M | +ve | −ve |
| 32 N.U.D | 29 | F | +ve | −ve |
| 33 N.U.D | 72 | F | +ve | −ve |
| 34 N.U.D | 29 | M | +ve | −ve |
| 35 N.U.D | 22 | F | +ve | −ve |
| 36 D.U | 28 | M | +ve | −ve |
| 37 D.U | 54 | M | +ve | −ve |
| 38 N.U.D | 44 | F | +ve | −ve |
| 39 N.U.D | 56 | F | +ve | −ve |
| 40 N.U.D | 40 | M | +ve | −ve |
| 41 N.U.D |  | M | +ve | −ve |
| 42 N.U.D | 65 | F | +ve | −ve |
| 43 G.U/D.U | 53 | F | +ve | −ve |
| 44 N.U.D | 43 | M | +ve | −ve |
| 45 N.U.D | 73 | F | +ve | −ve |
| 46 N.U.D |  | F | +ve | −ve |
| 47 N.U.D | 46 | F | +ve | −ve |
| 48 N.U.D | 41 | M | +ve | −ve |
| 49 N.U.D | 46 | F | +ve | −ve |
| 50 N.U.D | 34 | M | +ve | −ve |
| 51 N.U.D | 58 | F | +ve | −ve |
| 52 N.U.D | 51 | F | +ve | −ve |
| 53 N.U.D | 23 | M | +ve | −ve |
| 54 N.U.D | 54 | F | +ve | −ve |
| 55 D.U | 59 | F | +ve | −ve |
| 56 P.P.U | 31 | M | +ve | −ve |
| 57 O.U | 56 | M | +ve | −ve |
| 58 N.U.D | 33 | M | +ve | −ve |
| 59 PREV G.U | 78 | M | +ve | −ve |
| 60 N.U.D | 63 | M | +ve | −ve |
| 61 N.U.D | 27 | M | +ve | −ve |
| 62 N.U.D | 45 | F | +ve | −ve |
| 63 N.U.D | 38 | M | +ve | −ve |
| 64 N.U.D | 36 | M | +ve | −ve |
| 65 N.U.D | 66 | F | +ve | −ve |
| 66 N.U.D | 70 | F | +ve | −ve |
| 67 P.P.U | 66 | F | +ve | −ve |
| 68 D.U | 37 | F | +ve | −ve |
| 69 N.U.D | 64 | M | +ve | −ve |
| 70 N.U.D | 45 | M | +ve | −ve |
| 71 N.U.D | 24 | F | +ve | −ve |
| 72 N.U.D | 46 | M | +ve | −ve |
| 73 N.U.D | 53 | F | +ve | −ve |
| 74 N.U.D | 33 | M | +ve | −ve |
| 75 N.U.D | 30 | M | +ve | −ve |
| 76 N.U.D | 42 | F | +ve | −ve |
| 77 D.U | 36 | M | +ve | −ve |
| 78 N.U.D | 64 | F | +ve | −ve |
| 79 D.U | 34 | M | +ve | −ve |
| 80 N.U.D | 65 | F | +ve | −ve |
| 81 N.U.D | 56 | M | +ve | +ve* |
| 82 N.U.D | 42 | M | +ve | −ve |
| 83 N.U.D | 43 | F | +ve | −ve |
| 84 N.U.D | 75 | F | +ve | −ve |
| 85 N.U.D | 62 | F | +ve | −ve |
| 86 N.U.D | 64 | F | +ve | −ve |
| 87 N.U.D | 51 | M | +ve | −ve |
| 88 N.U.D | 39 | M | +ve | −ve |
| 89 N.U.D | 39 | F | +ve | −ve |
| 90 N.U.D | 40 | M | +ve | −ve |
| 91 N.U.D | 34 | F | +ve | −ve |
| 92 N.U.D | 60 | M | +ve | −ve |
| 93 N.U.D | 59 | M | +ve | −ve |
| 94 N.U.D | 67 | M | +ve | −ve |
| 95 N.U.D | 60 | F | +ve | −ve |
| 96 N.U.D | 38 | M | +ve | −ve |
| 97 N.U.D | 53 | M | +ve | +ve* |
| 98 N.U.D | 51 | M | +ve | −ve |
| 99 N.U.D | 54 | M | +ve | −ve |
| 100 N.U.D | 56 | M | +ve | −ve |

*indicates failure to cure infection.
D.U = Duodenal ulcer
P.P.U = Pre-pyloric ulcer
N.U.D = Non-ulcer dyspepsia
O.U = Oesophageal ulcer
G.U = Gastric ulcer Histological Changes The effects of therapy on histological grading of C. pylori density as well as lymphocyte and neutrophil infiltration are summarized in FIG. 2.

Histological scores have been arbitrarily assigned to show graphically the time-course of inflammation resolution. All patients presented initially with high scores for both chronic and active gastritis. Neutrophil infiltration disappeared rapidly parallelling C. pylori clearance. Lymphocyte infiltration, on the other hand, persisted for a much longer time.

This study has demonstrated that high (>90%) initial "clearance" of gastric C. pylori is possible with a combination of available antimicrobial agents. Such a high level of initial clearance has not been previously achieved. It is also clear that therapeutic success measured at the eight week biopsy, should for the present be termed "clearance". The term "eradication" should be reserved for patients remaining free of CP beyond six months. In this study most of those patients cleared of CP at eight weeks remained clear of the infection for more than twelve months.

Although C. pylori is susceptible to numerous antibiotics in vitro, such agents notoriously fail to eradicate it in vivo. Bismuth appears to be an important component in the combination chemotherapy. While it is not clear why several antimicrobials are required to improve eradication of CP, antibiotic access to the bacteria may be a problem. The bismuth compound may be required locally within the gastric pits and mucus whereas the antibiotics could be required to be carried systemically to reach bacteria deep in gastric pits and within endocytotic vacuoles. Presence of multiple strains of C. pylori with varying antibiotic susceptibility spectra could provide another explanation for the need to employ multiple antibiotics. In view of the multiplicity of strains, it is in fact surprising that such a high CP clearance rate could be achieved employing only two systemic antimicrobials and one locally-acting agent (CBS). Perhaps the success can be further explained by prevention of the development of resistant strains seen after short courses of single systemic antibiotics.

A clinically useful method for successful long term *C. pylori* eradication has not previously been described. Twelve month follow up figures of 51% and 35% have been reported using bismuth plus a single antibiotic. Such therapy would clearly be unsatisfactory for patients and may lead to creation of resistant *C. pylori* strains. It is also desirable to have an effective eradication therapy for *C. pylori* before embarking upon a double-blind trial designed to demonstrate the relevance of the organism in a particular disease.

Although it is known that bismuth can decrease tetracycline bioavailability, the antibiotic combination as used here achieved its desired effect in spite of presumed chelation. It would appear that adequate bismuth and tetracycline remained post-chelation to reach the infected targets. It is known also that chelation is in part pH dependent and low pH protects against chelation. As some patients with *C. pylori* infection will have impaired gastric acid secretion, elevated pH may have contributed to treatment failures. Other sources of treatment failure could include reduction in tetracycline bioavailability by ingestion of milk, antacids, iron or food, or simply non-compliance.

We claim:

1. A method of preventing recurrence of gastric ulcer associated with *Campylobacter pylori* (*Helicobacter pylori*) infection in a patient suffering from gastric ulcer disease associated with *Campylobacter pylori* (*Helicobacter pylori*) infection, said method comprising administering to said patient *Campylobacter pylori* infection eradicating amounts of pharmaceutically acceptable bismuth compound, first antibiotic selected from the group consisting of tetracycline and penicillins, and second antibiotic which is metronidazole.

2. A method as set forth in claim 1 further comprising a step of administering to said patient an effective amount of a gastric acid suppressant for a predetermined length of time.

3. The method as set forth in claim 2 wherein said predetermined length of time is three to twenty-eight days followed by an administration of said bismuth compound/antibiotics combination.

4. The method as set forth in claim 2 wherein said gastric acid suppressant is an histamine$_2$-receptor antagonist.

5. The method as set forth in claim 2 wherein said gastric acid suppressant is a benzimidazole.

6. The method as set forth in claim 5 wherein said benzimidazole is lansoprazole or omeprazole.

7. The method as set forth in claim 2 wherein said gastric acid suppressant is a prostaglandin.

8. The method as set forth in claim 2 wherein said gastric acid suppressant is a proton pump inhibitor.

9. The method as set forth in claim 2 wherein said gastric acid suppressant is a K/Na ATP-ase inhibitor.

10. A method of treating a patient with gastric ulcer associated with *Campylobacter pylori* (*Helicobacter pylori*) infection, said method comprising administering to said patient acid suppressant in an amount effective to obtain symptomatic relief and ulcer epithelialization before or during administering to said patient of *Campylobacter pylori* (*Helicobacter pylori*) infection eradication amounts of pharmaceutically acceptable bismuth compound, first antibiotic selected from the group consisting of tetracycline and penicillins, and second antibiotic which is metronidazole.

11. A method as set forth in claim 10 further comprising a step of administering to said patient an effective amount of a gastric acid suppressant for a predetermined length of time.

12. The method as set forth in claim 11 wherein said predetermined length of time is three to twenty-eight days followed by an administration of said bismuth compound/antibiotics combination.

13. The method as set forth in claim 11 wherein said gastric acid suppressant is an histamine$_2$-receptor antagonist.

14. The method as set forth in claim 11 wherein said acid suppressant is a benzimidazole.

15. The method as set forth in claim 14 wherein said benzimidazole is either lansoprazole or omeprazole.

16. The method as set forth in claim 11 wherein said gastric acid suppressant is a prostaglandin.

17. The method as set forth in claim 11 wherein said gastric acid suppressant is a proton pump inhibitor.

18. The method as set forth in claim 11 wherein said gastric acid suppressant is a K/Na ATP-ase inhibitor.

19. A method of preventing recurrence of duodenal ulcer associated with *Campylobacter pylori* (*Helicobacter pylori*) infection in a patient suffering from duodenal ulcer disease associated with *Campylobacter pylori* (*Helicobacter pylori*) infection, said method comprising administering to said patient *Campylobacter pylori* (*Helicobacter pylori*) infection eradicating amounts of a pharmaceutically acceptable bismuth compound, a first antibiotic selected from the group consisting of tetracycline and penicillins and a second antibiotic which is metronidazole and further comprising a step of administering to said patient an effective amount of a gastric acid suppressant for a predetermined length of time.

20. The method as set forth in claim 19 wherein said predetermined length of time of administration of said gastric acid suppressant is three to twenty-eight days followed by an administration of said bismuth compound/antibiotics combination.

21. The method as set forth in claim 19 wherein said gastric acid suppressant is an histamine$_2$-receptor antagonist.

22. The method as set forth in claim 19 wherein said acid suppressant is a benzimidazole.

23. The method as set forth in claim 22 wherein said benzimidazole is either lansoprazole or omeprazole.

24. The method as set forth in claim 19 wherein said gastric acid suppressant is a prostaglandin.

25. The method as set forth in claim 19 wherein said gastric acid suppressant is a proton pump inhibitor.

26. The method as set forth in claim 19 wherein said gastric acid suppressant is a K/Na ATP-ase inhibitor.

27. A method of treating a patient with duodenal ulcer associated with *Campylobacter pylori* (*Helicobacter pylori*) said method comprising administering to said patient a gastric acid suppressant in an amount and for a time effective to obtain symptomatic relief and ulcer epithelialization before or during administering to said patient of *Campylobacter pylori* (*Helicobacter pylori*) infection eradicating amounts of a pharmaceutically acceptable bismuth compound, a first antibiotic selected from the group consisting of tetracycline and penicillins and a second antibiotic which is metronidazole, thereby to cause healing of said duodenal ulcer as well as to prevent recurrence thereof.

28. The method as set forth in claim 27 wherein said predetermined length of time of administration of said gastric acid suppressant is three to twenty-eight days followed by an administration of said bismuth compound/ antibiotics combination.

29. The method as set forth in claim 27 wherein said gastric acid suppressant is an histamine$_2$-receptor antagonist.

30. The method as set forth in claim 27 wherein said acid suppressant is a benzimidazole.

31. The method as set forth in claim 28 wherein said benzimidazole is either lansoprazole or omeprazole.

32. The method as set forth in claim 27 wherein said gastric acid suppressant is a prostaglandin.

33. The method as set forth in claim 27 wherein said gastric acid suppressant is a proton pump inhibitor.

34. The method as set forth in claim 27 wherein said gastric acid suppressant is a K/Na ATP-ase inhibitor.

* * * * *